US008168173B2

(12) United States Patent
Crihan et al.

(10) Patent No.: US 8,168,173 B2
(45) Date of Patent: May 1, 2012

(54) CERCAN: AN ENERGY SUPPLEMENT PRODUCT FOR BOOSTING THE IMMUNE SYSTEM

(76) Inventors: Ioan G Crihan, New York, NY (US);
Geoffrey G Woods, Fairfield, CT (US);
Jerrold E. Hyams, New York, NY (US)

( * ) Notice: Subject to any disclaimer, the term of this patent is extended or adjusted under 35 U.S.C. 154(b) by 472 days.

(21) Appl. No.: 12/078,670

(22) Filed: Apr. 3, 2008

(65) Prior Publication Data
US 2009/0252813 A1    Oct. 8, 2009

(51) Int. Cl.
*A23L 1/05* (2006.01)
*A23L 1/30* (2006.01)
*A23L 1/31* (2006.01)
*A23L 3/26* (2006.01)
*A23L 3/015* (2006.01)
*A01N 63/00* (2006.01)
*A01N 65/00* (2009.01)

(52) U.S. Cl. ....... 424/93.7; 426/240; 426/575; 426/641; 426/648; 426/665

(58) Field of Classification Search .................. None
See application file for complete search history.

(56) References Cited

U.S. PATENT DOCUMENTS 6,399,105 B1 * 6/2002 Collin ........................... 424/550
6,455,013 B1 * 9/2002 Crihan ........................... 422/186
2009/0252813 A1 * 10/2009 Crihan et al. ................. 424/548

OTHER PUBLICATIONS

Derwent English Abstract: 2007-646904, Abstract only; 2007.*
Derwent English Abstract: 2002-140591, Abstract only; 2002.*
Derwent English Abstract: 2006-222681, Abstract only; 2006.*
"Quick View Gamma Radiation Technology", MEGARAD, Inc. brochure, at least before Aug. 8, 2006, p. 1-16.
"Quick View Gamma Radiation Technology", MEGARAD, Inc. revised Sep. 19, 2002, online brochure, http://megaradinc.tripod.com/index.htm of Aug. 12, 2003,, pp. 1-16.
"Quick View Gamma Radiation Technology", MEGARAD, Inc. revised Aug. 24, 2003, online brochure, http://magaradinc.tripod.com, pp. 1-16.
"Countries Using Irradiation to Sterilize Food", listing, at least before Aug. 8, 2006, p. 1.
Countries Using Irradiation (with Gamma) to Sterilize Organic Material, listing, at least before Aug. 8, 2006, p. 1-8.
"Irradiation Levels and Effects", listing, at least before Aug. 8, 2006, pp. 1-2.
"Gamat", http://en.wikipedia.org/wiki/Gamat online search, printed May 6, 2010, pp. 1-2.
"Sea Cucumber", http://en.wikipedia.org/wiki/Sea_cucumber_(food) online search, printed Jul. 25, 2010, p. 1.
"Gamt: The Traditional Healer from the Sea", http//www.langkawi-beaches.com/langkawai-gamat.html online search, printed May 6, 2010, pp. 1-3.
"Holothuroidea", http://tolweb.org/Hulothuroidea online search, printed May 5, 2010, pp. 1-3.
"Sea Cucumber", http://itmonline.org/arts/seacuke.htm. online search, printed May 2, 2010, pp. 1-2.
"Sea Cucumber", http://fao.org/docrep/007/y5501e/y5501e0b.htm online search, printed May 2, 2010, pp. 1-6.
"Sea Cucumber", http://www.gne-trading.com/learn_cucumber.html online search, printed May 6, 2010, pp. 1-4.
Sea Cucumber:, http://hubpages.com/hub/greenextkudus online search, printed May 6, 2010, p. 1.
"Sea Urchins", http://www.insbioscience. com/ins_bio/health_cucumber.html online search, printed May 6, 2010, p. 1.
"Sea Urchins", http://microscopy-uk.org.uk/mag/artjul00/urchin1.html. online search May 5, 2010, p. 1.
"Sea Urchins", http://google.com/images online search, printed May 6, 2010, p. 1-6.
"Sea Urchins",http://en.wikipedia.org/wiki/Sea_urchin online search, printed Jul. 25, 2010, pp. 1-2.
"File: Yokohoma Chinese Mdicine Shark fin etc.jpg", http://en.wikipedia.org/wiki/File: Yokohama_Chinese_Medicine _Shark_fin_etc.jpg online search, printed Jul. 25, 2010, pp. 1-2.
"Shark Fin Soup", http://en.wikipedia.org/wiki/Shark_fin_soup online search, printed Jul. 25, 2010, p. 1.
"Sponge", http://en.wikipedia.org/wii/Sea_sponge online search, printed Jul. 25, 2010, p. 1.
"Calcium Carbonate", http://en.widipedia.org/wiki/Calcium_carbonate online search Jul. 25, 2010, pp. 1-2.
"Skeleton", http://en.wikipedia.org/wiki/Sea_sponge online search Jul. 25, 2010, p. 1.
"Sargassum", http://en.1wikipedia.org/wiki/Sargassum online search Jul. 25, 2010, p. 1.
"Immunity (medical)", http://en.wikipedia.org/wiki/Immunity_(medical) online search, printed Jul. 28, 2010, pp. 1-2.
"Immunology", http://en.wikipedia.org/wiki/Immunilogy online seaerch, printed Jul. 28, 2010, p. 1.
"Historical examination of the immune system", http://en.wikipedia.org/wiki/Immunology online search, printed Jul. 28, 2010, p. 1.
"Pathogen", http://en.wikipedia.org/wiki/Pathogen online search, printed Jul. 28, 2010, pp. 1-2.
"Clinical immunology", http://en.wikipedia.org/wiki/Immunology online search, printed Jul. 28, 2010; p. 1.
"Cytokine", http://en.wikipedia.org/wiki/Cytokine online search, printed Jul. 28, 2010, p. 1.
"Interleuin", http://en.wikipedia.org/wiki/Interleukin online search, printed Jul. 28, 2010, p. I.
"Interferon", http://en.wiki/pedia.org/wiki/ Interferon online search, printed Jul. 28, 2010, p. 1.
"Peptide bond formation", http://en.wiki/pedia.org/wiki/ Interferon online search, printed May 6, 2010, p. 2.
"Sea Sponges", http://www.google.co/images?um=1&hl=en&tbs=isch%3A1&sa=1g=sea+sponges&ag . . . online search, printed May 6, 2010, p. 1.

* cited by examiner

*Primary Examiner* — Debbie K Ware
(74) *Attorney, Agent, or Firm* — Merek, Blackmon & Voorhees, LLC

(57) ABSTRACT

This invention concerns the process of creating an energy supplement product, good also as an anti-aging, aphrodisiac and as an alternative source to prevent or to remedy some diseases. The product is a composition of five ingredients: four marine animals (sea cucumber, sea urchin, sea sponge, and shark fin), and an algae called Sargassum. These ingredients are sterilized and then dried by using isothermal isotopes, reduced to powder, measured and encapsulated.

10 Claims, 1 Drawing Sheet

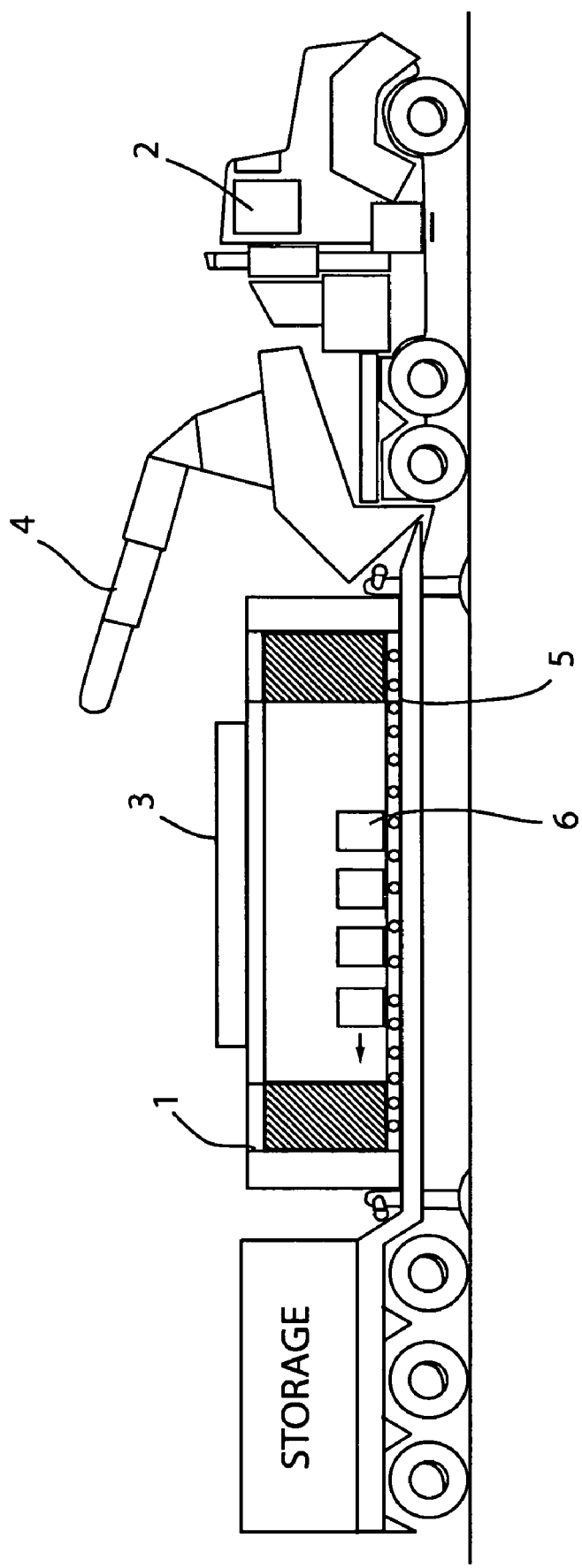

CERCAN: AN ENERGY SUPPLEMENT PRODUCT FOR BOOSTING THE IMMUNE SYSTEM

CROSS REFERENCE TO RELATED APPLICATIONS

This application claims the benefit of U.S. Provisional Application 60/836,131, filed Aug. 8, 2006.

BRIEF DESCRIPTION OF THE DRAWINGS

FIG. 1 shows a side plan view of a transportable trailer having a drawing tractor.

DETAILED DESCRIPTION

This invention concerns the process of producing an energy supplement product, good also as an anti-aging, as aphrodisiac and as alternative source for preventing or remedy some diseases. It is based on four marine animals: sea cucumber (Gamat variety), sea sponge, sea urchin (red but also green), shark fin, and a seaweed called Sargassum. The ingredients produced by these marine elements are sterilized and then dried by using isothermic isotopes, transformed into powder, measured, and then introduced into capsules.

All of the ingredients aforementioned are a good source of energy. The sea cucumber, specifically the golden variety type called "Gamat" provides many vitamins (A, B1 or thiamine, B2 or riboflavin, B3 or niacin, C and E) and minerals (calcium, manganese, iron, magnesium, potassium). A good source of vitamins and minerals is also the algae called Sargassum. The only non-edible element, the sea sponge, is rich in calcium.

It is also believed they help prevent and fight various diseases, such as cancer (sea sponges), or aging (sea cucumber and sea urchin). A similar product exists already on the market with the ingredients transformed into jelly and put into plastic containers. The containers are kept and transported in refrigerators. The disadvantage of the refrigeration is that, in case of interruption of electricity, the jelly is thawed. The re-refrigeration of the thawed product is in this case dangerous for the consumer. Besides the danger of thawing, the containers with jelly are difficult to be used by individuals during trips, or other occasions.

DESCRIPTION OF THE DRAWING

FIG. 1 shows a transportable trailer 1 having a drawing tractor 2 for bringing the irradiation chamber which is suitably housed in a clad housing to a sterilization and drying site. The trailer has a removable protective roof 3 which may be removed by a crane 4 in order to load or unload the radioisotope source 3. The trailer has a roller conveyor system 5 upon which containers 6 are moved into and out of the irradiation chamber in a timed sequence for a preselected dwell time in the irradiation chamber. The dwell time can be such as to ensure that each container and its contents receive between 1 million and 5 million RADs.

The invention claimed is:

1. A method of producing an energy supplement product, comprising:
   a) providing a mixture, the active ingredients of the mixture consisting essentially of Sargassum seaweed, Gamat sea cucumber, sea sponge skeleton, shark fin, and one of the group of red sea urchin gonads and green sea urchin gonads; and
   b) sterilizing and drying the mixture with isothermic isotopes in a device comprising an irradiation chamber to form the energy supplement product.

2. The method of claim 1, wherein said mixture is sterilized by irradiation in a mobile, wheeled metal chamber.

3. The method of claim 1, wherein said mixture is sterilized by irradiating with one million to five million rads.

4. The method of claim 3, further comprising:
   c) converting the mixture of step b) into a powder.

5. A method of producing an energy supplement product comprising:
   a) forming a mixture of Sargassum seaweed, Gamat sea cucumber, sea sponge skeleton, shark fin, and one of the group of red sea urchin gonads and green sea urchin gonads;
   b) sterilizing and drying the mixture of step a) with isothermic isotopes in an irradiating chamber;
   c) converting the mixture of step b) into a powder; and
   d) encapsulating the powder of step c) to produce an energy supplement product.

6. The method of claim 5, wherein said mixture is sterilized by irradiation with one million to five million rads.

7. The method of claim 5, wherein said irradiating chamber is in a mobile, wheeled metal housing.

8. A method of producing an energy supplement product comprising:
   a) providing a mixture consisting of Sargassum seaweed, Gamat sea cucumber, sea sponge skeleton, shark fin, and one of the group of red sea urchin gonads and green sea urchin gonads;
   b) sterilizing and drying the mixture with isothermic isotopes in an irradiating chamber;
   c) converting the mixture of step b) into a powder; and
   d) encapsulating the powder of step c) to produce an energy supplement product;
   wherein said energy supplement is capable of boosting an immune system in an individual.

9. The method of claim 8, wherein said mixture is sterilized by irradiation with one million to five million rads.

10. The method of claim 8, wherein said irradiating chamber is in a mobile, wheeled metal housing.

\* \* \* \* \*